US012594318B1

(12) United States Patent　　　(10) Patent No.:　US 12,594,318 B1

Gonzalez-Ulloa　　　(45) Date of Patent:　Apr. 7, 2026

(54) SYSTEM AND METHOD FOR MANUFACTURING A POLICOSANOL-RICH GRANULATED SUGAR CANE JUICE PRODUCT

(71) Applicant: Jorge Enrique Gonzalez-Ulloa, Ocala, FL (US)

(72) Inventor: Jorge Enrique Gonzalez-Ulloa, Ocala, FL (US)

(73) Assignee: THE CANE JUICE COMPANY, LLC, Jupiter, FL (US)

( * ) Notice: Subject to any disclaimer, the term of this patent is extended or adjusted under 35 U.S.C. 154(b) by 654 days.

(21) Appl. No.: 17/985,126

(22) Filed: Nov. 10, 2022

Related U.S. Application Data

(63) Continuation-in-part of application No. 17/750,128, filed on May 20, 2022, now abandoned, which is a continuation-in-part of application No. 16/702,238, filed on Dec. 3, 2019, now Pat. No. 11,357,815, which is a continuation of application No. 16/163,365, filed on Oct. 17, 2018, now Pat. No. 10,493,121, which is a continuation-in-part of application No. 15/803,037, filed on Nov. 3, 2017, now Pat. No. 10,632,167.

(60) Provisional application No. 63/191,009, filed on May 20, 2021.

(51) Int. Cl.
　*A61K 36/899*　　(2006.01)
　*A23L 2/04*　　(2006.01)
　*A23L 2/72*　　(2006.01)
　*A23L 2/82*　　(2006.01)
　*A23L 33/105*　　(2016.01)
　*A61K 9/00*　　(2006.01)
　*A61K 31/045*　　(2006.01)
　*C07C 29/74*　　(2006.01)
　*C13B 10/00*　　(2011.01)
　*C13B 10/02*　　(2011.01)
　*C13B 50/00*　　(2011.01)

(52) U.S. Cl.
　CPC ............. *A61K 36/899* (2013.01); *A23L 2/04* (2013.01); *A23L 2/72* (2013.01); *A23L 2/82* (2013.01); *A23L 33/105* (2016.08); *A61K 9/0095* (2013.01); *A61K 31/045* (2013.01); *C07C 29/74* (2013.01); *C13B 10/003* (2013.01); *C13B 10/02* (2013.01); *C13B 50/00* (2013.01); *A23V 2002/00* (2013.01); *A61K 2236/15* (2013.01); *A61K 2236/31* (2013.01); *A61K 2236/333* (2013.01); *A61K 2236/39* (2013.01); *A61K 2236/51* (2013.01)

(58) Field of Classification Search
　None
　See application file for complete search history.

*Primary Examiner* — Russell G Fiebig

(74) *Attorney, Agent, or Firm* — Glenn Gold, P.A.; Glenn E. Gold

(57)　　　　　ABSTRACT

A method for processing sugar cane juice from raw sugar cane stalks to produce various forms of a natural sugar cane juice product preserves policosanols naturally occurring in the raw sugar cane stalks, resulting in policosanol-rich natural sugar cane juice-based products such as a dry, granulated sweetener concentrate.

4 Claims, 14 Drawing Sheets

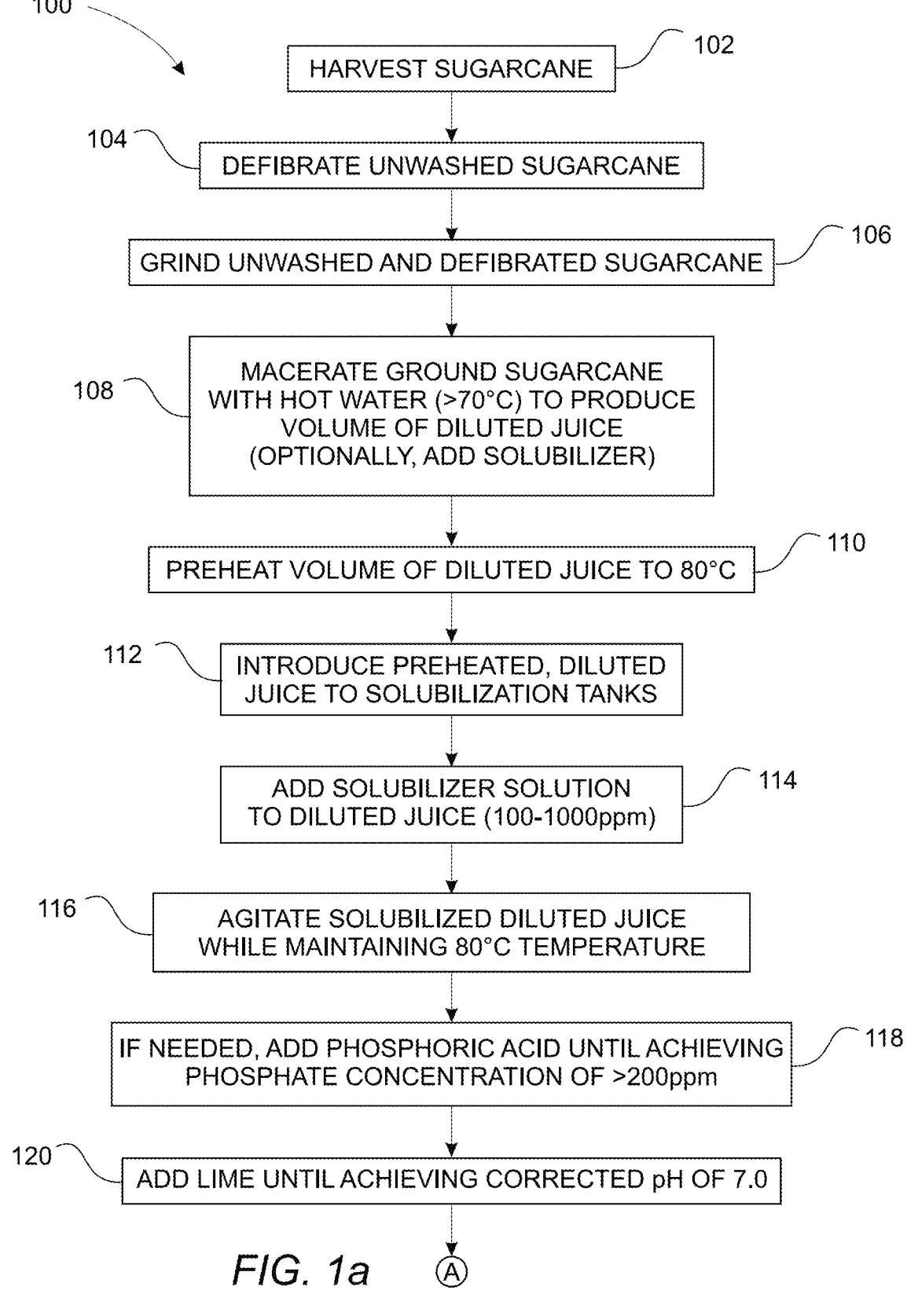
FIG. 1a    Ⓐ

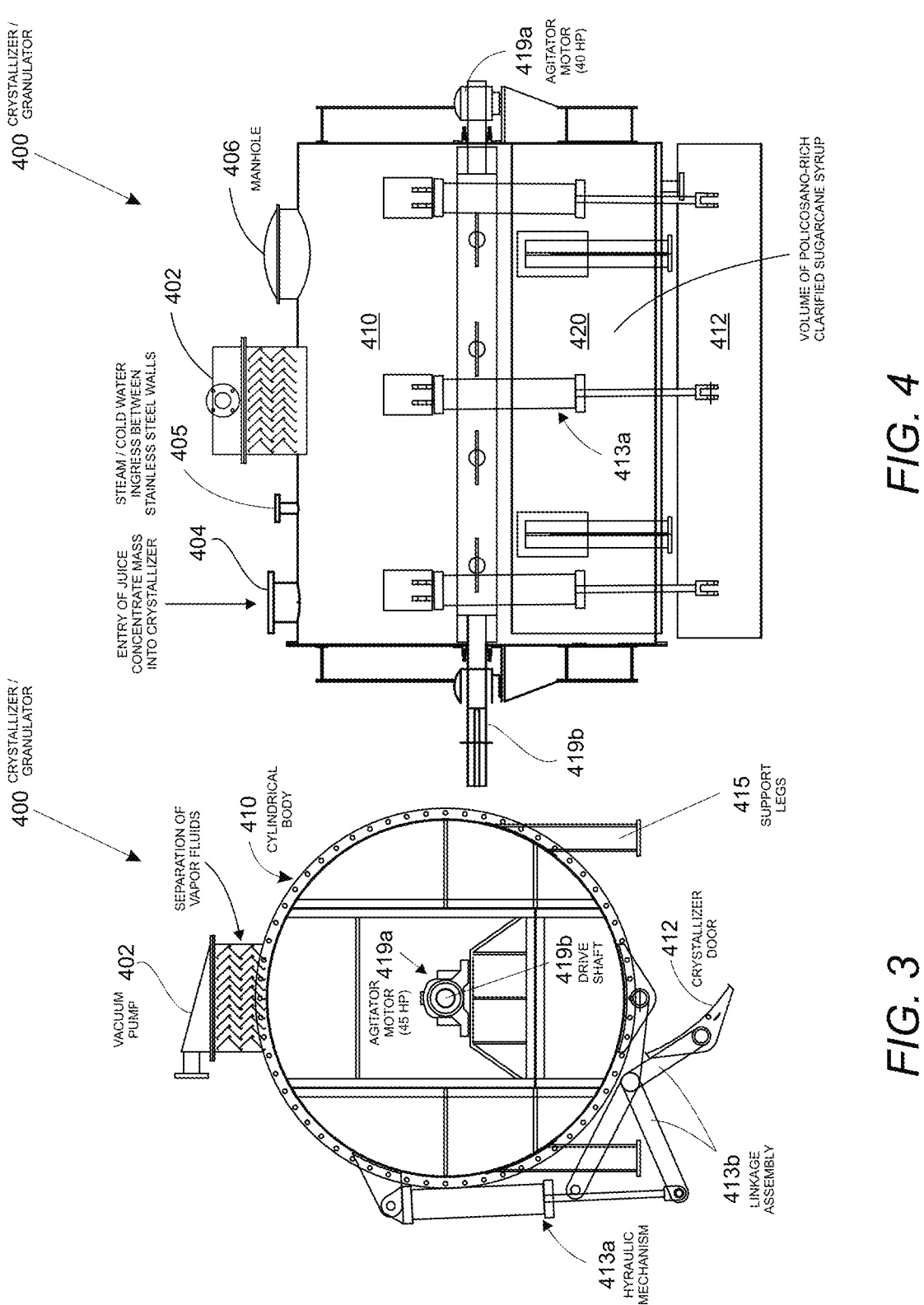

400 CRYSTALLIZER / GRANULATOR

419a AGITATOR MOTOR (40 HP)

406 MANHOLE

402

STEAM / COLD WATER INGRESS BETWEEN STAINLESS STEEL WALLS

405

410

420

412

VOLUME OF POLICOSANO-RICH CLARIFIED SUGARCANE SYRUP

413a

ENTRY OF JUICE CONCENTRATE MASS INTO CRYSTALLIZER

400 CRYSTALLIZER / GRANULATOR

SEPARATION OF VAPOR FLUIDS

402

410 CYLINDRICAL BODY

VACUUM PUMP

AGITATOR MOTOR (45 HP) 419a

419b DRIVE SHAFT

412 CRYSTALLIZER DOOR

415 SUPPORT LEGS

413b LINKAGE ASSEMBLY

413a HYRAULIC MECHANISM

*FIG. 3*

PREPARATION OF SOLUBILIZER

STIRRER /AGITATOR
(SOLUBILIZATION TANK)
320

326
324
322

326
324
322

CRYSTALLIZER OUTER
CYLINDRICAL BODY

410

CRYSTALLIZER
LOWER DOOR

412

POLICOSANOL-RICH
GRANULATED PRODUCT

SCREW
CONVEYOR

500

DRYER SYSTEM 600

DRYER CYLINDER 610

INTERIOR SURFACE FINS 624

DRYER CYLINDER INTERIOR SURFACE 622

620

DRYER CYLINDER INTERIOR

DRYER CYLINDER 610

SYSTEM AND METHOD FOR MANUFACTURING A POLICOSANOL-RICH GRANULATED SUGAR CANE JUICE PRODUCT

CROSS-REFERENCE TO RELATED APPLICATIONS

This U.S. non-provisional patent application is a continuation-in-part (CIP) of U.S. patent application Ser. No. 17/750,128, filed on May 20, 2022, which claims priority to U.S. provisional patent application No. 63/191,009, filed May 20, 2021, and which is a continuation-in-part (CIP) of U.S. patent application Ser. No. 16/702,238 (now U.S. Pat. No. 11,357,815), which is a continuation (CON) of U.S. patent application Ser. No. 16/163,365 (now U.S. Pat. No. 10,493,121), which is a continuation-in-part (CIP) of U.S. patent application Ser. No. 15/803,037 (now U.S. Pat. No. 10,632,167).

This application claims priority to each of the aforementioned patent applications. The entire contents of each of the aforementioned patent applications is hereby incorporated-by-reference herein.

FIELD OF THE INVENTION

The present invention relates generally to sugar cane processing. More specifically, the invention pertains to large-scale, industrial processing of raw sugar cane to produce a high purity, policosanol-rich dry granulated sugar cane juice-based product.

BACKGROUND OF THE INVENTION

The production of crystallized sugar from raw sugar cane is well known. Furthermore, the development of equipment and associated processes for producing sugar from sugar cane stalks has been extensive. Generally, sugar product is produced from a naturally occurring liquid contained within the plant cells of raw sugar cane stalks.

The present applicant, in his issued U.S. Pat. No. 6,245, 153 (the '153 patent), the entire contents of which are incorporated-by-reference herein, disclosed an improved method for processing raw sugar cane to produce a consumable sugar cane juice, which overcame significant shelf-life limitations of then state-of-the-art sugar cane processing methods. Prior to applicant's aforementioned patented invention, there were no known methods for efficiently producing a high-purity natural sugar cane juice product having an adequate shelf life to support commercial distribution. In his '153 patent, the present applicant taught a novel method for producing a stabilized natural sugar cane juice product having an adequate shelf life to enable commercial distribution, without requiring addition of unnatural chemical additives during juice processing.

Subsequently, the present applicant, in his issued U.S. Pat. No. 10,632,167 (the '167 patent) and U.S. Pat. No. 10,493, 121 (the '121 patent), the entire contents of which are incorporated-by-reference herein, taught improved methods for large scale, industrial processing of raw sugar cane, to produce shelf-stable natural sugar cane juice-based products having a high purity, while preserving extracted policosanols occurring naturally in epicuticular sugar cane stalk wax. The epicuticular sugar cane stalk wax is a waxy white outer layer of the sugar cane stalk, which is composed of long chain waxy alcohols, aldehydes and their esters. The mix of waxy alcohols ranging from 20 carbons and higher are known as Policosanols. The '167 and '121 patents disclosed systems and methods enabling the production of highly pure, highly (shelf) stable juice-based products in various forms (e.g., a consumable beverage, a viscous syrup concentrate, etc.), wherein the sugar cane juice products incorporate policosanols extracted from the raw sugar cane, and subsequently retained during their manufacture. The patented methods lay out a process for maximizing the extraction of the natural policosanols from the raw sugar cane stalk, and subsequently maximizing their preservation throughout the production of the sugar cane juice-based products.

Policosanol is well-known to aid in lowering blood cholesterol level. More recently, several studies have reported the physiological activities of policosanol, such as anti-inflammatory effects, antioxidant effects, and lowering of the incidence of ageing-related diseases (e.g., hypertension, stroke, etc.) as well described by Jang, Kim, Han and Jung in Natural Product Sciences, 25 (4): 293-297 (2019) ("Physiological Activities of Policosanol Extracted from Sugarcane Wax). As the myriad health benefits of policosanols have become increasingly well-recognized, there has been a growing desire in many industries (e.g., the pharmaceutical industry, the supplement/nutraceutical industry, the cosmetics industry, and the food & beverage industry) to find ways to efficiently and cost-effectively incorporate policosanols into their respective products (i.e., pharmaceuticals, supplements/nutraceuticals, cosmetics, and food & beverage products). Conventionally, policosanol is directly extracted from the epicuticular wax of sugar cane and other plant waxes (e.g., beeswax, cereal grains, grasses, leaves, fruits, nuts, seeds, etc.) using organic solvents, such as hexane, benzene, heptane, xylene, octane, kerosene, toluene, ethanol, etc. These conventional processes are relatively complex, costly, and often require the use of toxic chemicals. For these and other reasons, it would be highly desirable to provide a method of processing sugar cane on an industrial scale to produce a policosanol-rich sugar cane juice product in a dry, powdered/granulated form conducive for use as an additive.

Non-centrifuged cane sugars (NCS) containing policosanols are known. For example, Kokuto, a non-centrifuged Okinawan cane brown sugar manufactured by slow cooking sugar cane juice, has been found to contain a relatively high concentration of policosanols. However, Kokuto is produced using a manual open pan heating system, which does not let itself to industrial scale manufacture. Consequently, the cost of Kokuto (i.e., USD $20 to 25/lb.) is approximately 100-times the cost of conventional refined sugar (i.e., USD $0.22 to $0.25/lb.). Furthermore, Kokuto and similar products are mainly produced in a solid block form, rather than as dry granules. The solid block form is not conducive for use in applications where small, consistent, measurable quantities of policosanol additive is desired during the manufacture of the final products. Accordingly, a solid block is not a convenient form from which a policosanol additive can be derived. Instead, it would be much more desirable to incorporate policosanol in a granular, or powdered, dry form that is homogenous. That is, where the quantity, or concentration, of policosanols in the individual grains, or crystals, has adequate uniformity to enable a specific, measurable quantity of policosanols to be incorporated into the final product based primarily upon the volume or weight of the additive. In other words, in a form where the policosanol content can be easily measured based on the weight or volume of the additive.

There have been recent efforts to increase the policosanol content of granular brown sugar by adding wax extract from defatted rice bran and rice bran oil to achieve granulated sugars containing policosanol. However, it would be much more beneficial to provide a means for processing raw sugar cane to produce a dry, granulated sugar product retaining the policosanols contained in the raw sugar cane (i.e., as opposed to extracting policosanol-rich wax from raw materials, and subsequently adding the extracted wax during production of the dry, granulated sugar product).

In his prior patents, the present applicant disclosed methods for preserving the policosanols in raw sugar cane during the production of shelf-stable, sugar cane juice-based products. More recently, the present applicant has derived a modified version of his prior sugar cane processing methods, which provides further improved extraction and subsequent preservation of policosanols during production of a dry granulated form of the natural sugar cane juice-based product (as well as non-dry sugar cane juice-based products such as sugar cane syrup concentrate).

For various reasons, sugar cane mills around the world have been experiencing sharp declines in production and profitability. Significantly, the sugar cane processing system(s) taught herein can be easily and inexpensively integrated with conventional sugar cane processing mills to enable mill owners to cost-effectively convert their mills to manufacture, as an alternative to conventional refined sugar, a more healthy, high policosanol content (i.e., PC≥200 mg/kg) dry, granulated natural sugar cane juice-based product in accordance with the method(s) of the present invention. Significantly, demand for healthier sweeteners and sugar alternatives—such as those produced in accordance with the present methods—is growing while the corresponding demand for conventional refined sugar is in decline, the cost to produce high PC sweeteners in accordance with the inventive method(s) is on par with the cost to produce conventional refined sugar, and the potential profitability associated with producing high PC sweeteners according to the present invention, is significantly greater than that associated with the production of conventional refined sugar.

BRIEF DESCRIPTION OF THE DRAWINGS

FIGS. 1a-1c present a flow chart of a method for manufacturing a high policosanol content dry, granulated sugar cane juice-based product in accordance with at least one implementation of the present invention;

FIG. 3 is a right side/end elevation view of a general schematic diagram of a crystallization apparatus 400 used in connection with the system and method of the present invention;

FIG. 4 is a front side elevation view of the crystallization apparatus 400 introduced in FIG. 3;

FIG. 12a is a photographic image (open end view) of the cylindrical body 410 of the crystallizer apparatus 400 of the present invention;

FIG. 12b is a photographic image (closed end view) of the cylindrical body 410 of the crystallizer apparatus 400 shown in FIG. 12a;

DETAILED DESCRIPTION

As used herein, the terms Degrees Brix (°Bx) and Brix Percent (% Brix) are meant to denote a measure of the total soluble solids content (i.e., total dissolved solids) of an aqueous solution. Generally, the soluble solids are mostly sugars. One degree Brix (1°Bx), or one-percent Brix (1% Brix), is defined as 1 gram of soluble solids in 100 grams of an aqueous solution. Therefore, a solution that is 50% Brix is equal to 50% soluble solids.

As used herein, the term Juice Brix refers to the total solids (i.e., sugars and non-sugars) content present in the raw sugar cane juice. Brix measurements of raw sugar cane are typically conducted in the field using a hand refractometer (HR). Different types of sugar cane can differ greatly in their sucrose levels; HR Brix of raw sugar cane typically varies from 15% to 23%.

As used herein, the term Juice Sucrose Percent is meant to denote the actual cane sugar present in the juice. It is usually determined using a polarimeter; hence, Juice Sucrose Percent is alternatively referred to as Pol Percent. A sugar crystal is very close to 100% sucrose.

Purity Coefficient refers to the percentage of sucrose present in the total solids content in the juice (i.e., since raw sugar cane also includes non-sucrose components, such as reducing sugars, organic acids, amino acids, proteins, starch, gums, coloring matter, and other suspended matter). A higher purity indicates the presence of higher sucrose content out of the total solids present in the juice.

Purity Percentage ("Apparent Purity") is equal to (Pol Percent/HR Brix)*100. With regard to conventional commercial cane sugar processing, a cane crop is considered fit for harvesting if it has attained a minimum of 16% sucrose and 85% purity.

The present invention provides a system, and corresponding methods, for industrial-scale manufacturing of a dry granular sugar cane juice-based product in which the policosanol content naturally occurring in the epicuticular wax of the raw sugar cane stalks is extracted, and subsequently preserved throughout the manufacturing process.

Figure 1B:
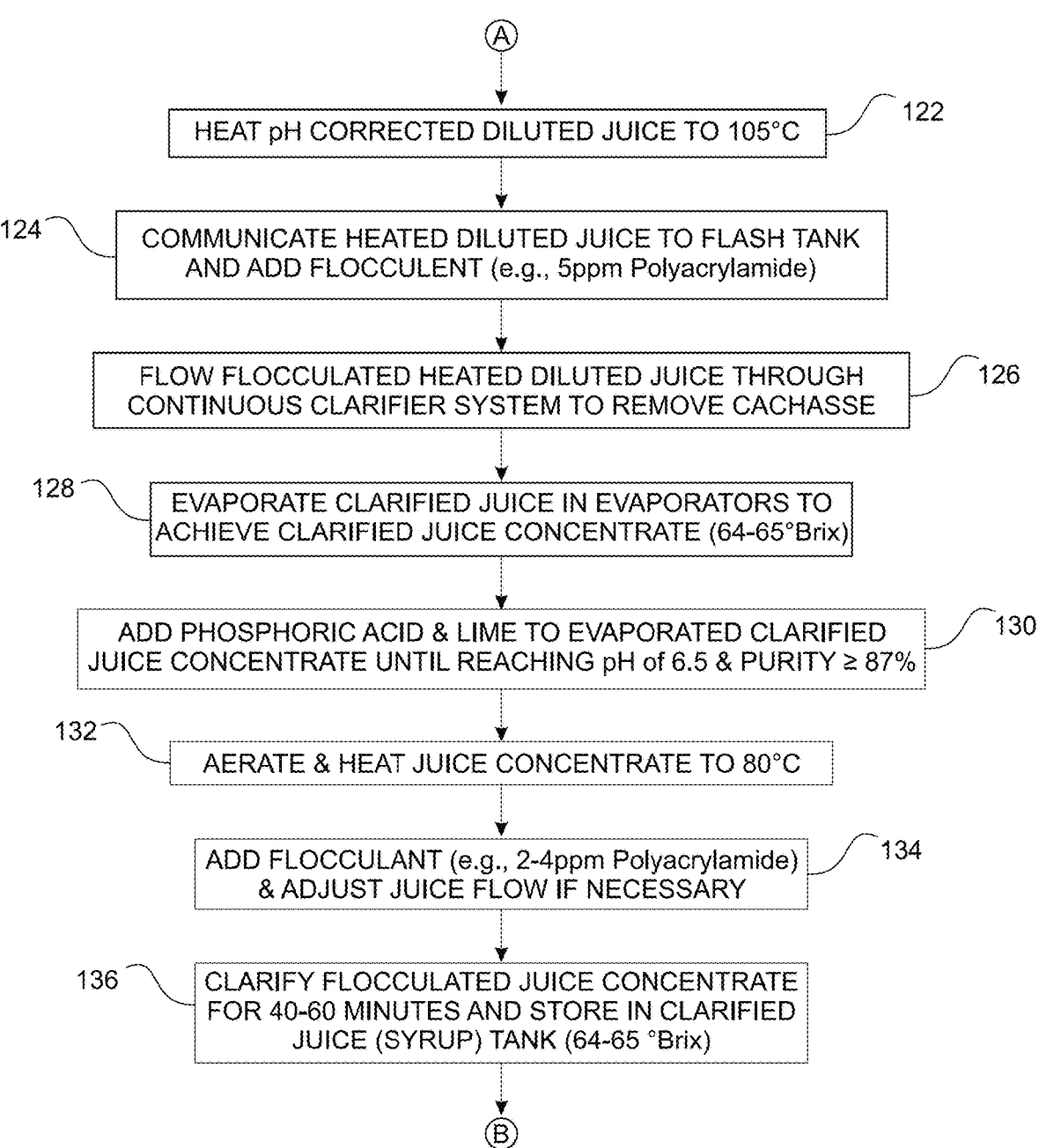
Figure 1C:
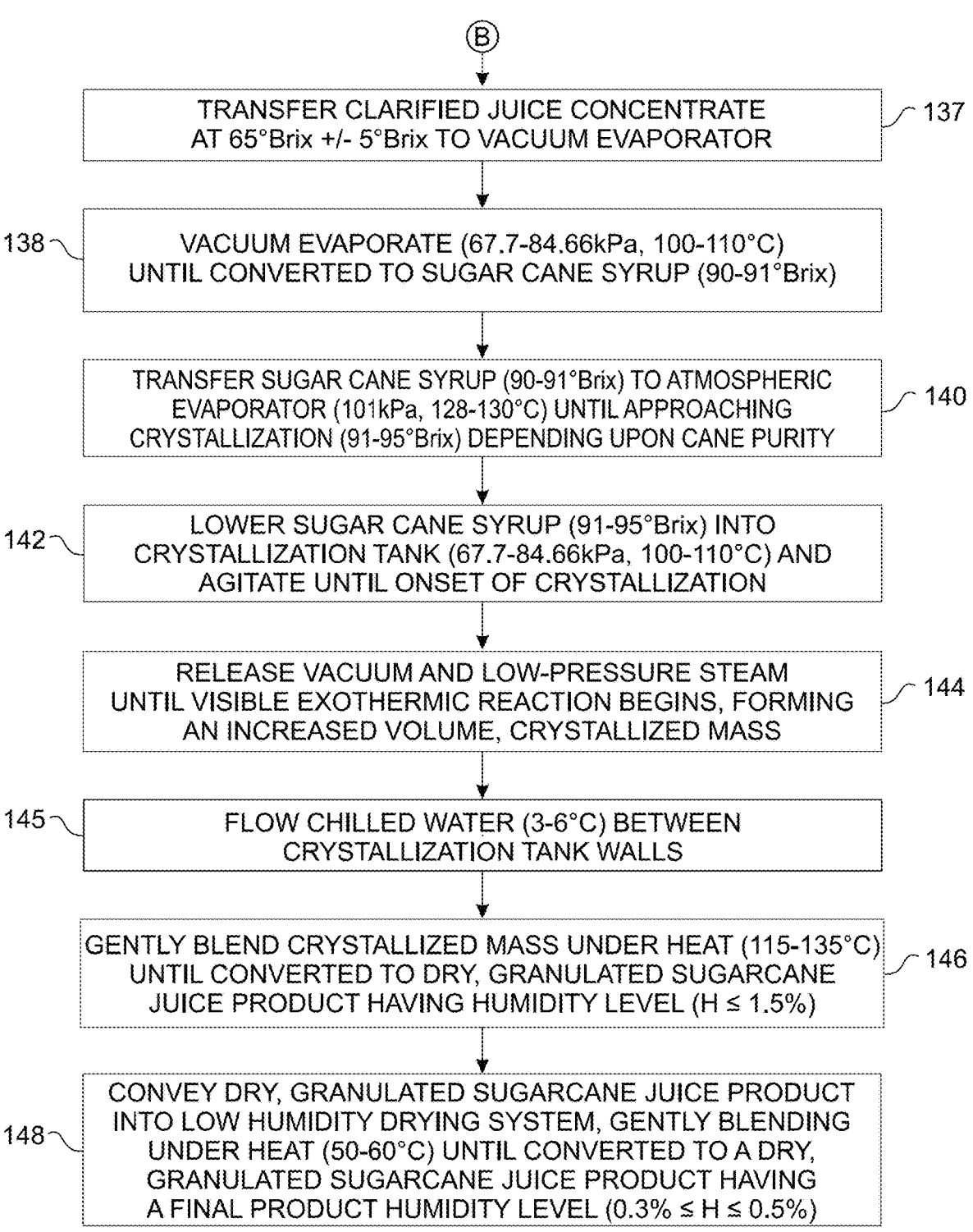
Figure 2:
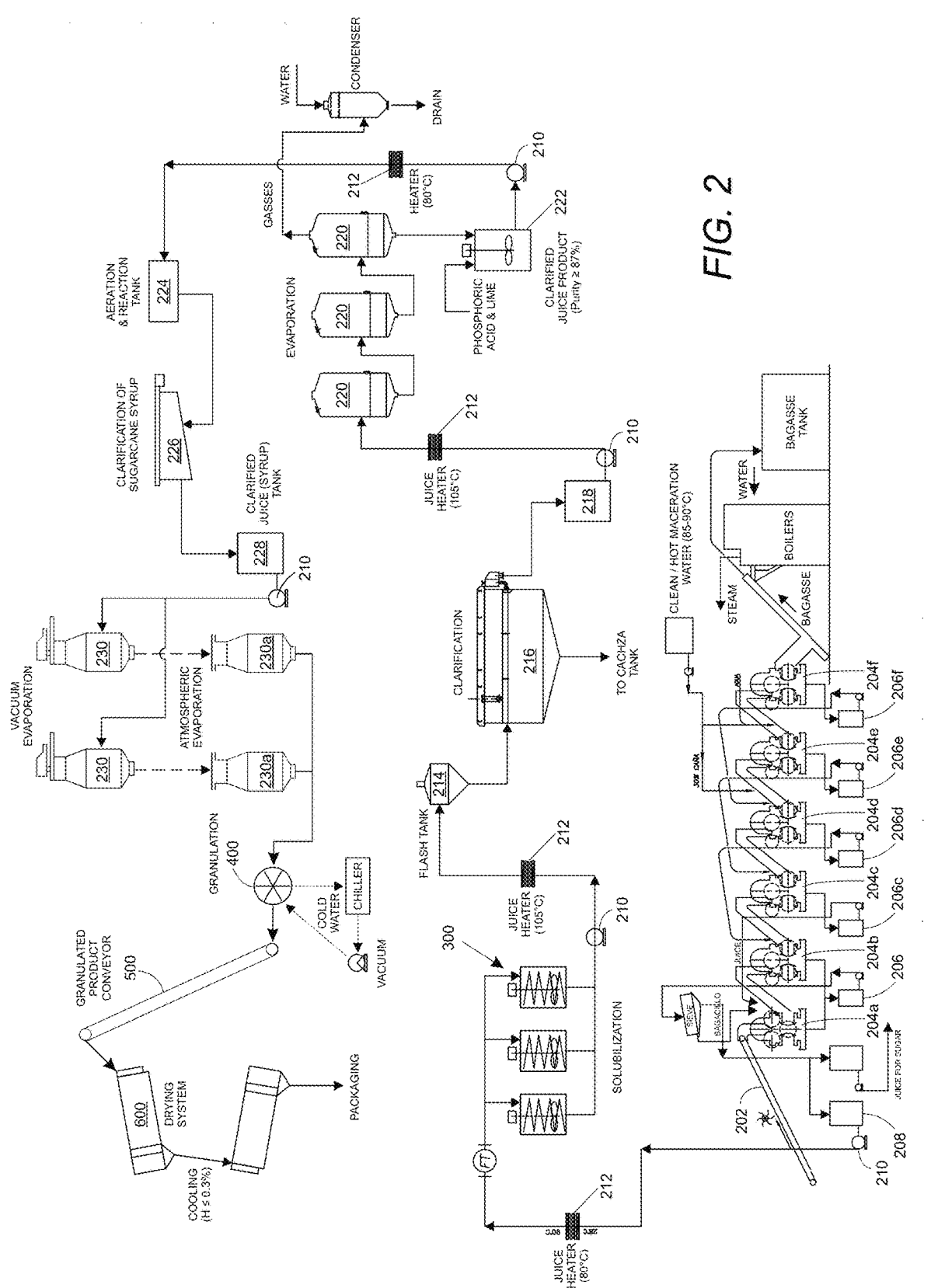
FIG. 2 is a general schematic diagram illustrating equipment and a corresponding method of use to produce a policosanol-rich, dry, granulated sugar cane juice-based product in accordance with at least one implementation of the present invention.

Referring initially to FIGS. 1a-1c in conjunction with FIG. 2, a method 100 for manufacturing a policosanol-rich dry granular sugar cane juice-based product is provided in accordance with an exemplary implementation of the present invention.

Initially, in step 102, harvested cane is achieved through a clean green cut. The cane must not contain any ripening agents and should preferably be about 12 to 13 months old. The sugar cane juice should have a Preparation Index (PI) of at least 85%, and preferably in the range of 89 to 90%. The PI test is carried out on a sample of shredded cane. The PI is the ratio of brix in the ruptured (i.e., open) cells to total brix in the cane. The PI may also denote the percentage of total cane cells that have been ruptured (i.e., opened) during shredding. The greater the PI, the greater the efficiency of the mill preparation for sucrose extraction will be. The percentage of cane plant cells which have been ruptured (i.e., opened) by the cane preparation equipment may be used as a measure of the effectiveness of the preparation equipment (e.g., cane shredder).

To avoid the need for sugar cane burning, it is preferred that the selected sugar cane is manually cut approximately two inches from the stool, removing all green and dry leaves. However, the sugar cane may be carefully harvested using conventional equipment without departing from the intended scope of the present invention. It is also preferable that the sugar cane tops, commonly referred to as "cogollos," are cut off; thereby avoiding the introduction of their pasty taste which is difficult to eliminate in processing without the use of chemical additives. It is crucial that the cut cane stalks are not cleaned at this step because the majority of policosanols in raw sugar cane are contained within the outer portion (or cortex) as an epicuticular wax containing upwards of 80 percent (80%) of the total policosanols in the raw sugar cane. Furthermore, if the cane is burned then the policosanols are evaporated, completely defeating the purpose of the invention. In step 104, the unwashed cut cane may be deposited on tables and subjected to a conventional defibrillation process.

Subsequently, in step 106, the unwashed, defibrillated, cut cane is transported via a conveyor 202 (FIG. 2) into a series of conventional sugar cane grinding mills 204a-204f (FIG. 2) where, as indicated by step 108, the ground cane is macerated with hot water having a temperature greater than 70° C., but preferably about 80° C. At this preferred maceration water temperature, the flow rate of the maceration water through the initial tandem of mills, 204a and 204b, should be approximately 25-30%—and most preferably 28%—greater than the corresponding flow rate of the sugar cane therethrough. It should be noted that higher maceration water temperatures could be used without departing from the intended scope of the invention; however, no appreciable benefit is derived using water heated above 80° C. Likewise, lower maceration water temperatures could be used without departing from the intended scope of the invention; however, no benefit is derived using lower water temperatures. Moreover, achieving adequate dilution using relatively higher and lower maceration water temperatures would necessitate changes in other processing variables (e.g., flow rate of cane through the mills, rates of agitation, etc.) which is not desirable.

During conventional sugar cane processing, sugars are dissolved and separated in water. However, waxy alcohols, due to their non-polar nature, are less soluble in water. Accordingly, the policosanol-rich epicuticular wax may not completely dissolve out of the sugar cane and into the water simply by using hot water. Depending upon the quality of the raw sugar cane being processed (e.g., sucrose content, purity, etc.), it may not be absolutely necessary to completely dissolve all of the epicuticular wax out of the sugar cane. However, in some instances it is necessary to dissolve more of the epicuticular wax out of the raw sugar cane than is possible using hot maceration water alone.

In that regard, the present inventor has discovered that introducing a volume of an effective solubilizer during the maceration process aids in more completely dissolving the policosanol-containing epicuticular wax out of the raw sugar cane. In particular, an amphiphilic compound, or surfactant, may be added immediately before a first mill 204a (FIG. 2) of the series of mills to more effectively dissolve the policosanol-containing wax into the hot maceration water. Optionally, surfactant may also be introduced immediately prior to one or more of the other ones 204b-204f of the series of mills.

Surfactants are amphiphilic molecules that have hydrophobic and hydrophilic parts; namely, hydrophilic tail groups that repels water, and a hydrophilic head groups that attract (i.e., mix/dissolve in) water. Surfactants reduce the polar/non-polar repulsions between the wax and the water. When there are a sufficient amount of surfactant molecules present in a solution, the surfactant molecules self-assemble, or come together, to form structures called micelles. As the micelle forms, the surfactant heads position themselves such that they are exposed to the water, while the tails are grouped together in the center of the structure protected from the water. The behavior of the micelles is dependent upon the level of surfactants used. Increasing the surfactant level reduces the size of the micelles, which increases solubility. Decreasing the surfactant level increases the size of the micelles, which decreases solubility-creating an emulsion.

Accordingly, an "emulsifier" is simply a surfactant that stabilizes emulsions. Micelle on the order of micrometers (i.e., $10^{-6}$ meters) are considered to be emulsifiers, which are unstable and not water soluble. Micelle on the order of nanometers (i.e., $10^{-9}$ meters) are considered to be solubilizers, which are very stable and water soluble. Solubilized policosanol particles are on the order of approximately 200 nanometers (200 nm). Emulsified policosanol particles are on the order of approximately 5 micrometers (5 μm), or about 25-times the size of solubilized policosanol particles.

The hydrophilic head of each surfactant is electrically charged (i.e., negative, positive or neutral). Ionic surfactants are those that have hydrophilic groups that dissociate into an ionic group. Examples of ionic surfactants include the following: Sulfonates; Sulfates; Polyoxyethylene sulfates; Carboxylates; Phosphates; Ammonium; and Quaternary ammonium). Non-ionic surfactants are neutral, they do not have any charge on their hydrophilic end. For non-ionic groups, the hydrophilicity of the hydrophilic group comes from their ability to produce hydrogen bonds with water. Examples of non-ionic surfactants include the following: Polyoxyethylene (POE); Polyols; Sucrose esters; and Polyglycidyl esters. Examples of non-ionic surfactants that have proven highly effective solubilizing policosanols in the water-diluted sugar cane juice—under heat and agitation using a novel solubilizer apparatus 300 (FIGS. 7-11b)—include the following: Ceteareth–n (n=20, 25, 30); Polysorbate 20; and Polysorbate 80.

Although the initial sugar cane juice extraction step could be carried out without the addition of such surfactants, it is preferable to add surfactant during hot water maceration-particularly, where it is desirable to extract a greater percentage of policosanols from the raw sugar cane than is achievable using hot water alone. The present inventor has found that using hot water alone (i.e., absent any surfactant), approximately 70% of policosanols are extracted. However, with the addition of surfactant, upwards of 85% of policosanols may be extracted-resulting in approximately 600-800 ppm of policosanols in the diluted juice. At this stage of the process, the extracted policosanols remain suspended in the diluted juice (i.e., as an emulsion, wherein the policosanols are not completely solubilized). However, as described in greater detail herein, the present inventor has discovered a process for completely solubilizing the policosanol molecules in the diluted sugar cane juice.

The hydrophilic-lipophilic balance (HLB) of a surfactant is a measure of the degree to which it is hydrophilic or lipophilic, where hydrophilic refers to the ability of a substance to dissolve in water (or other hydrophilic solvents), and lipophilic refers to the ability of a substance to dissolve in lipids. For non-ionic surfactants, HLB=20*$M_h$/M, where $M_h$ is the molecular mass of the hydrophilic portion of the molecule, and M is the molecular mass of the whole molecule, giving a result on a scale of 0 to 20. An HLB value of 0 corresponds to a completely lipophilic-hydrophilic molecule, while a value of 20 corresponds to a completely hydrophilic/lipophobic molecule. In this manner, the HLB value can be used to predict the surfactant properties of a molecule.

For policosanol solubilization, HLB values greater than 14 are needed (i.e., HLB>14). Applicant has found that solubilization using the aforementioned surfactants (i.e., in conjunction with heating and agitation in novel solubilization tanks 300) has proven to be very stable to guard, or protect, the policosanol molecules from being separated, or extracted, out of the diluted sugar cane juice. In fact, the present inventor has found that even policosanol extraction with strong solvents such as formaldehyde was not possible after policosanol solubilization was achieved.

Significantly, the use of surfactants with HLB values greater than 14 (HLB>14) has proven extremely effective as a means of preserving policosanols in the sugar cane juice during processing in accordance with the present invention. Applicant has discovered that policosanol solubilization enables the diluted sugar cane juice to be exposed to extreme processing temperatures without evaporating, or otherwise destroying, the policosanols in the diluted sugar cane juice.

Subsequently, in step 110, the resulting volume of diluted juice 208 is communicated via pump 210 through preheaters 212 until reaching a preferred temperature of 80° C. Although the diluted juice 208 could be preheated to temperatures above 80° C., doing so does not result in the extraction of an appreciable amount of additional policosanols.

Subsequently, in step 112, the preheated volume of diluted juice is communicated to solubilization tanks 300 (FIGS. 2 and 7-11b) where it is subjected to solubilization in steps 114 and 116. Significantly, the step of solubilization is accomplished using a novel solubilization tank 300, which effectively solubilizes, or dissolves, the policosanols in the volume of diluted juice. That is, following solubilization, the policosanols are no longer suspended as an emulsion in the diluted juice.

Preferably, solubilization is accomplished using a solubilizer solution comprised of a solubilizer agent and hot water.

The solubilized diluted juice solution may have a solubilizer concentration in the range of 100 ppm (100 mg/L) to 1000 ppm (1000 mg/L) of solution, with the concentration preferably at the upper end of that range. Alternatively stated, the solubilizer concentration may be in the range of 0.01% to 0.1% of the solubilized, diluted sugar cane juice solution.

Figures 7, 8:
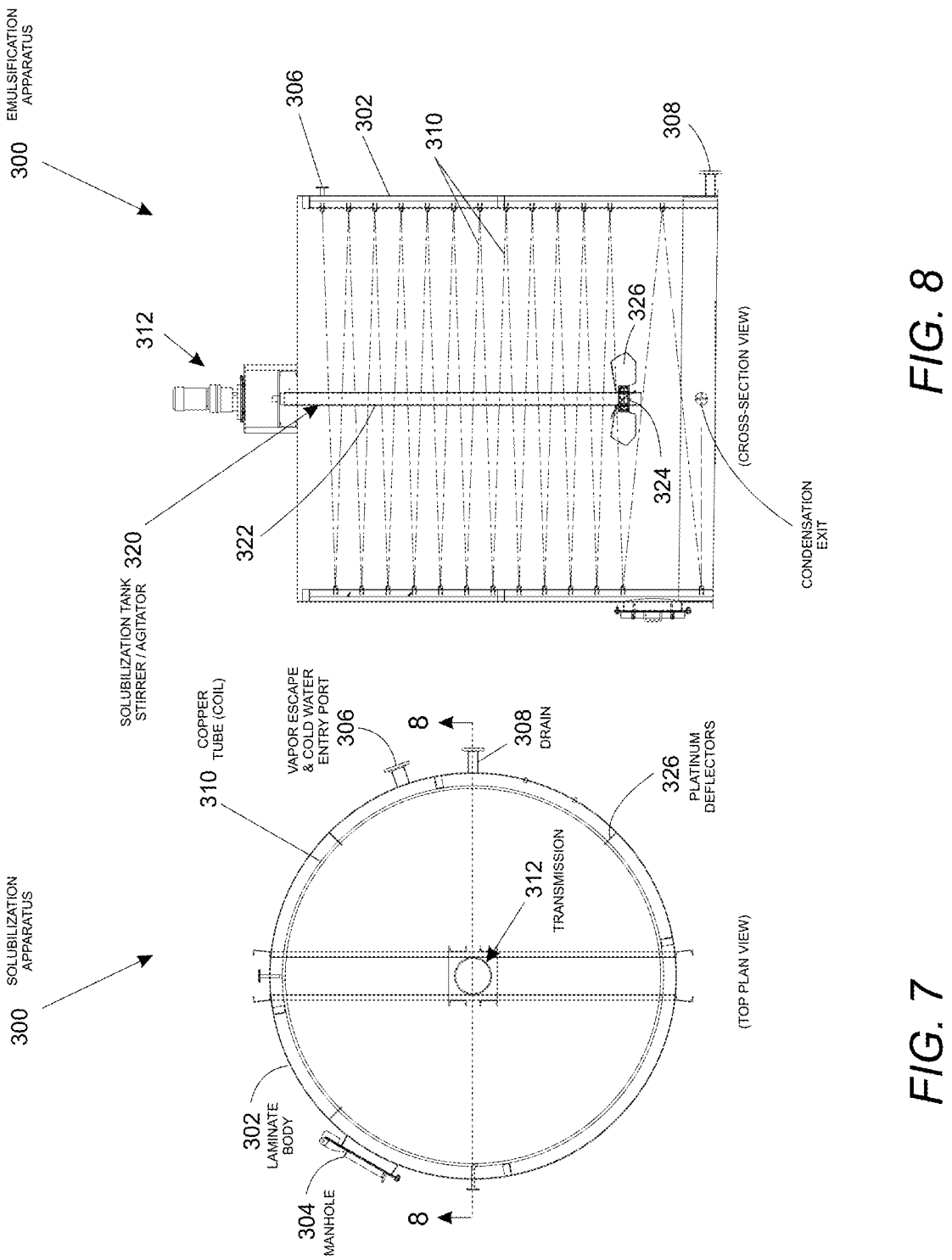
FIG. 7 is a top plan (schematic) view of a solubilization apparatus 300 used in connection with the system and method of the present invention.
FIG. 8 is a cross-sectional (schematic) side view of the solubilization apparatus 300 taken along section line 8-8 of FIG. 7.
Figure 9:
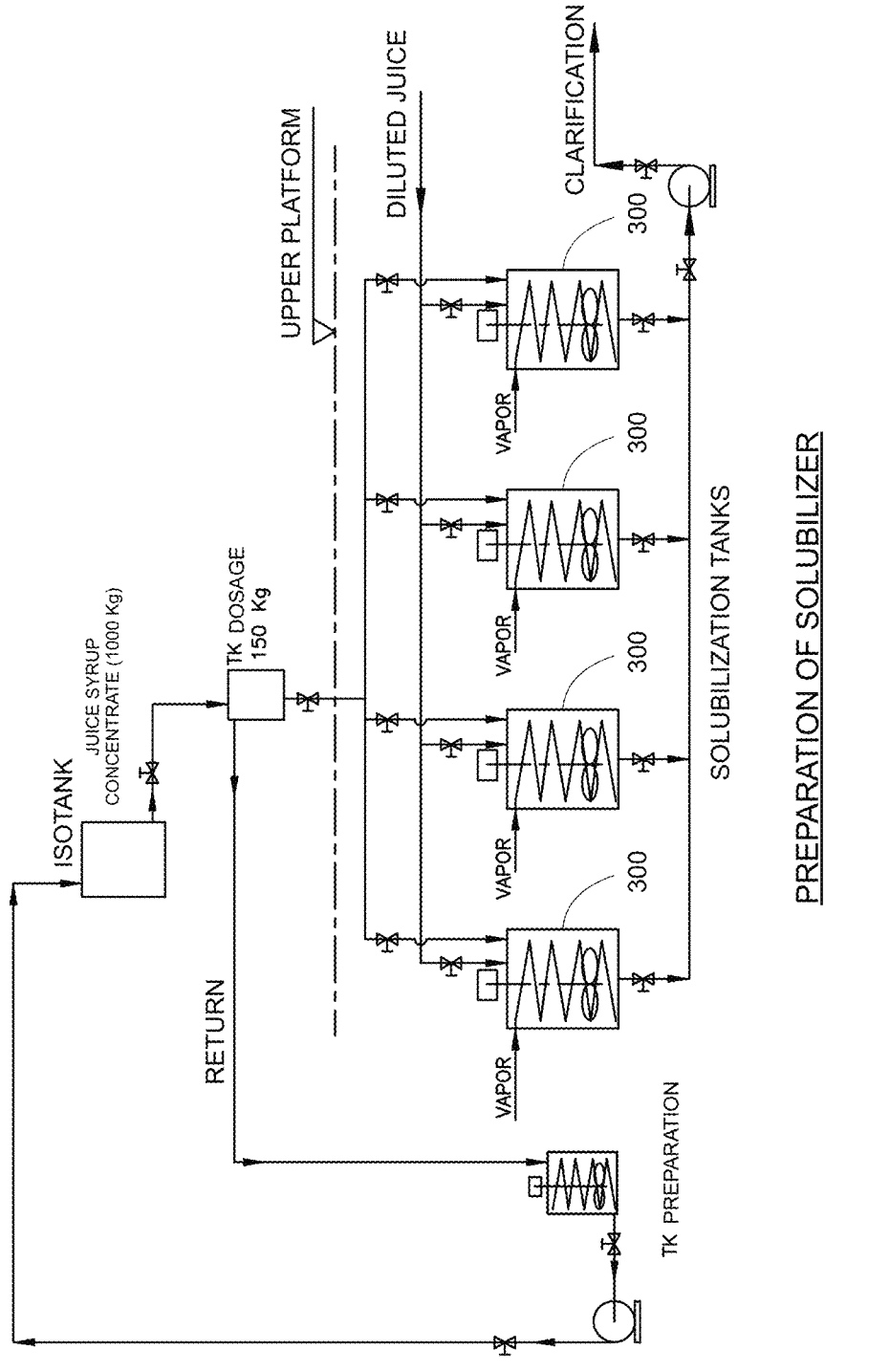
FIG. 9 is general schematic diagram of a solubilization sub-process of the method of the present invention.
Figure 10:
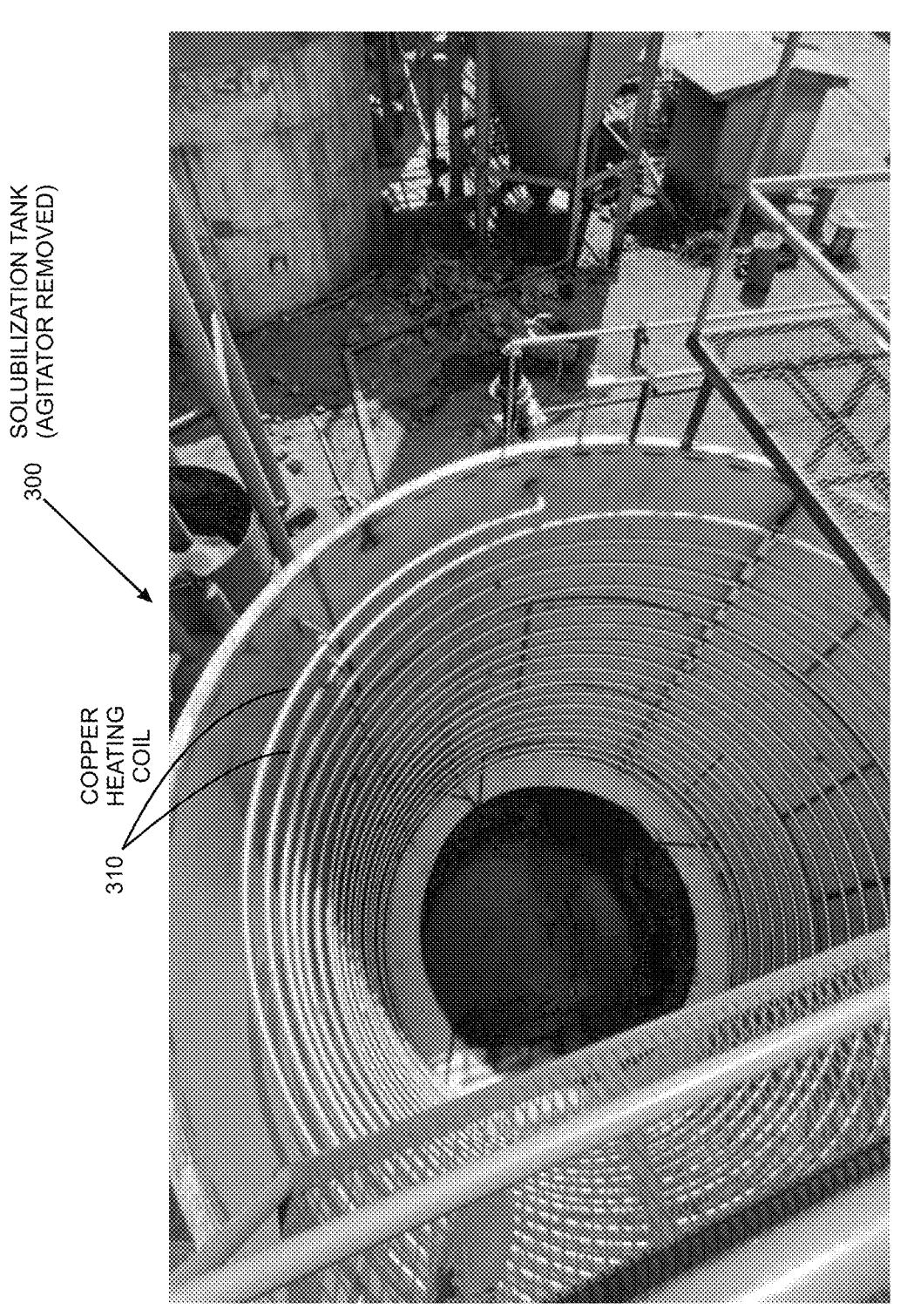
FIG. 10 is a photographic image of the interior of a solubilization apparatus/tank 300 used in connection with the present invention, with the agitator mechanism 320 removed to more clearly show the copper heating coils 310 disposed upon the interior surface thereof.
Figures 11A, 11B:
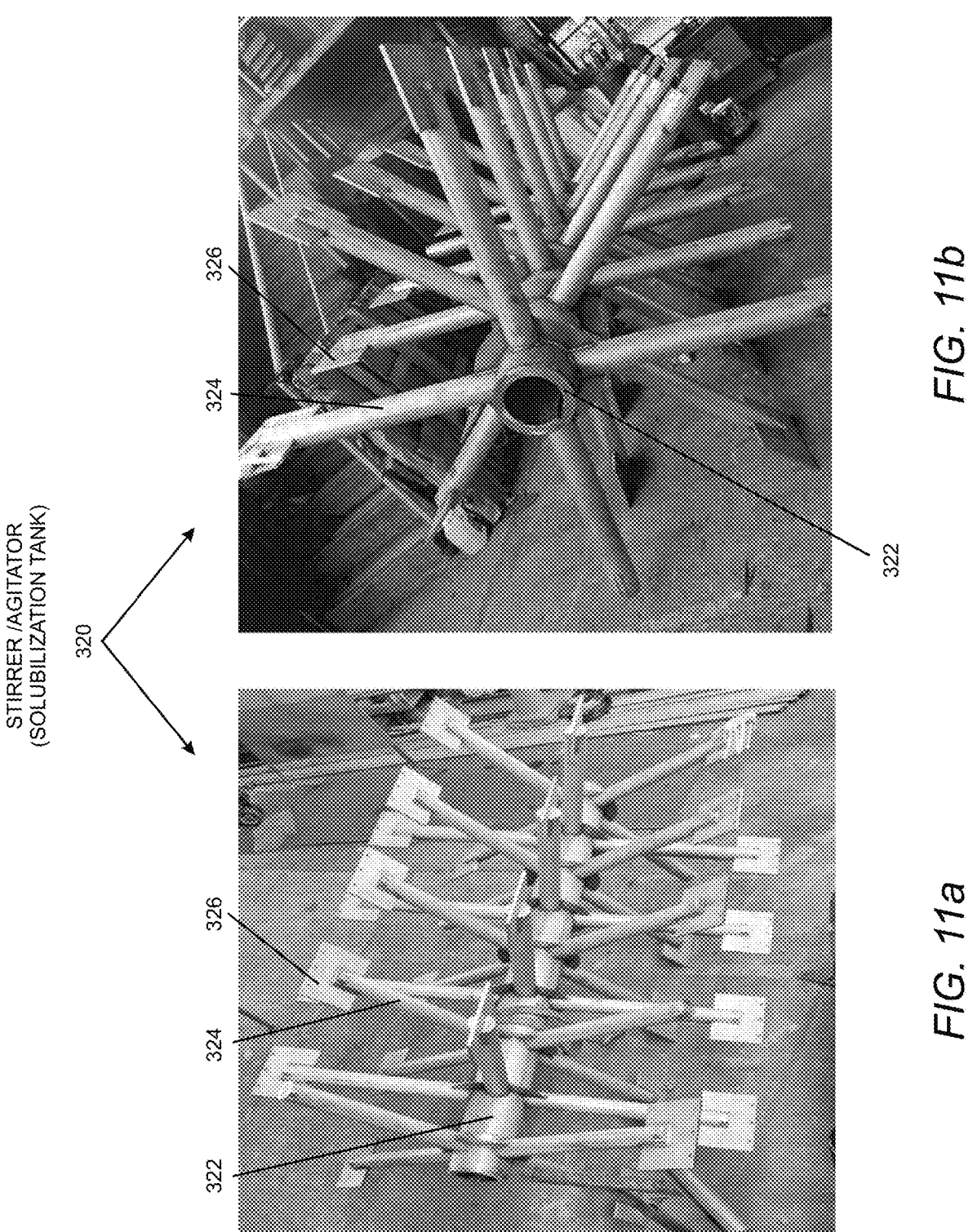
FIGS. 11a and 11b are photographic images (top and end perspective views) of the agitator (stirring) mechanism 320 isolated from the solubilization tank 300.
Figures 12A, 12B:
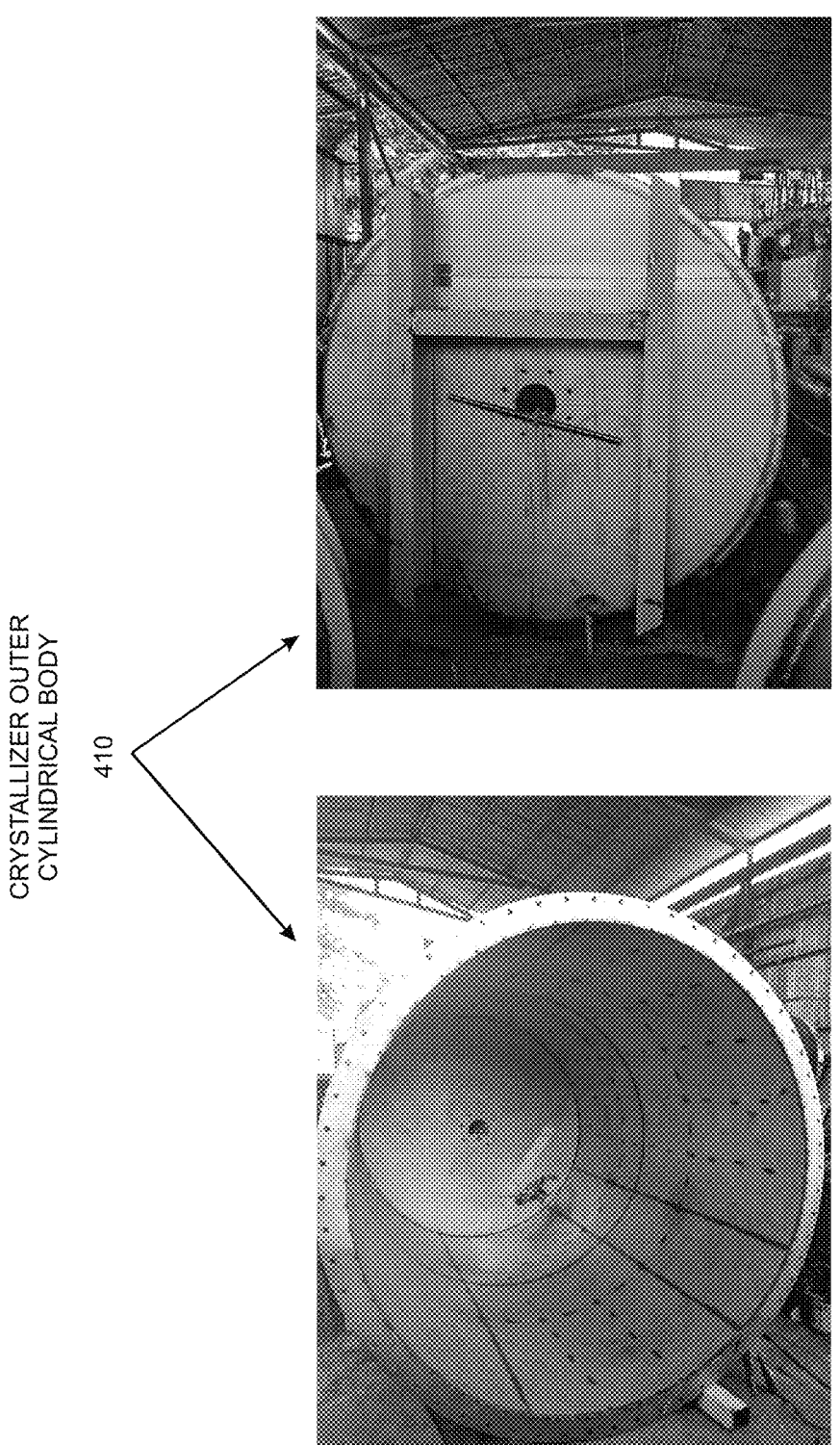

In step 116, the volume of diluted sugar cane juice and solubilizer is maintained at the preferred temperature of about 80° C., via a copper heating coil 310 (see FIGS. 8 and 10) and is continuously agitated via a rotating agitator 320 (see FIGS. 8 and 11a-11b). Along its length, rotating agitator 320 has a series of arms 324 extending radially outward from a central shaft 322, wherein each of the arms terminates distally at a deflector/paddle 326. Rotating agitator 320 is driven at an operating end by a transmission mechanism 312. The solubilizer and diluted sugar cane juice mixture should preferably be maintained at the preferred 80° C. temperature throughout this solubilization step. Significantly, the solubilizer tanks 300 incorporate deflectors 326 (or similar structural components) for generating the desired turbulent flow. The present inventor has found success maintaining the solubilizer and diluted juice mixture in agitation at an agitator rotation speed of 300 rotations per minute (300 RPM) for a period of at least 30 minutes, while maintaining the preferred 80° C. temperature. As previously noted, the solubilized policosanol molecules become very stable during subsequent processing. The present inventor has found that the solubilized policosanols become completely resistant to being extracted out of, or separated from, the diluted sugar cane juice even under extremely high processing temperatures.

Subsequently, in steps 118-126 the solubilized diluted sugar cane juice volume is subjected to an initial clarification process.

In step 118, following solubilization, phosphoric acid may be added until achieving a desired phosphate concentration of at least 200 ppm. If the phosphate concentration is below 200 ppm, the clarification will be poor. Accordingly, if the phosphate concentration is below 200 ppm, phosphoric acid may be added. On the other hand, if the phosphate concentration is at least 200 ppm it may not be necessary to add phosphoric acid to the solubilized, diluted sugar cane juice.

In step 120, a volume of milk of lime (i.e., Calcium Hydroxide), or lime, may be added to the juice until a preferred, corrected pH of 7.0 is attained. Once the preferred pH has been achieved (i.e., once the pH has been "corrected"), in step 122, the pH corrected solubilized volume of diluted sugar cane juice may be pumped through a system of heaters 212 to a preferred temperature of 105° C.

Subsequently, in step 124, the heated and pH corrected solubilized diluted sugar cane juice is flowed to a flash tank 214 containing a volume of flocculant. The flash tank 214 is open to the surrounding atmosphere where dissolved gasses in the juice are eliminated. It is important to eliminate entrained air from the juice to prevent undesirable effects, such as flocculant flotation. Furthermore, removal of compressed gasses, such as air, helps to maintain a constant temperature of the juice. The flocculant aids in forming flocs that will precipitate out, or settle, to the bottom of the continuous clarifier 216 during subsequent processing. The flocs are basically compounded by insoluble calcium phosphate that is formed from the reaction of milk of lime and inorganic phosphate present in the juice. As noted above, if the phosphate concentrations are below 200 ppm the clarification will be poor.

As will be apparent to those skilled in the art, there are at least 10-15 different commercially available flocculants that could be employed. As an example, the flocculant may be a volume of polyacrylamide comprising a concentration of about 5 ppm of the volume of diluted sugar cane juice.

Subsequently, in step 126, the flocculated, heated juice is communicated through the continuous clarifier system 216, where the Cachaza is separated out and removed (as described in great detail in applicant's aforementioned U.S. Pat. Nos. 10,632,167 and 10,493,121), and the remaining volume of clarified juice may be communicated to a clarified juice holding tank 218. Significantly, as noted in the '167 and '121 patents, the Cachaza is not discarded because it contains a rich concentration of policosanols that are beneficial to retain in the final product. Generally, the Cachaza may be communicated to special filters (e.g., vacuum belt filters) for further processing, wherein policosanol-containing juice is extracted from the Cachaza and communicated back to the solubilization tanks 300, where it is recombined with the sugar cane juice being processed. In particular, policosanols contained within the precipitate mud (i.e., containing heavier impurities) settling at the bottom of the clarifier, as well as policosanols contained within the impurity-rich foam froth floating on the juice surface at the top of the clarifier, are preferably subjected to vacuum press filtration to separate the undesirable impurities from the policosanol-rich sugar cane juice, and then reintroduced into the solubilizer tanks 300 for further processing. In this manner, policosanols that would normally be lost in the Cachaza are salvaged to further increase the policosanol content, or concentration, in the final sugar cane juice product.

In step 128, following initial clarification, the volume of clarified juice may be communicated (e.g., via pump 210) to one or more evaporators in order to evaporate water from the volume of clarified juice. The present inventor has found success using a system of triple-effect evaporators 220 to further concentrate the volume of clarified juice. Preferably, the volume of clarified juice is maintained within a temperature range of about 105° C. to 110° C. while in the first one of the evaporators 220, and within a cooler temperature range of about 70° C. to 75° C. while in the third one of the evaporators. Preferably, evaporation is continued until the remaining volume of clarified sugar cane juice is concentrated to at least about 65° Bx. Accordingly, following evaporation, the volume of diluted sugar cane juice is converted to a volume of initially clarified sugar cane juice concentrate, or syrup.

Subsequently, in steps 130-136, the volume of initially clarified juice syrup may be subjected to a further, or secondary, clarification process. Since the clarified juice syrup concentrate is very viscous, at about 65° Bx, secondary clarification is accomplished via a flotation process; as opposed to the initial clarification via precipitation/settling. The settling method would not be possible with juice syrup due to its high density and viscosity. The mechanism of syrup clarification involves the trapping of air bubbles within the flocs and intermolecular attraction across the air/liquid interface. Syrup clarification occurs by heating the syrup, then aerating it to trap the fine particles, which are finally coagulated by a low molecular weight flocculant. The scum, or froth, will then float to the top of the syrup clarifier 226 for removal.

In step 130, volumes of phosphoric acid and milk of lime, or calcium hydroxide, may be added to the volume of clarified juice syrup until achieving a volume of clarified juice syrup having a (preferred) pH of about 6.5 and a purity of at least about 87%.

Subsequently, in step 132, the pH-corrected volume of clarified juice syrup may be communicated to an aeration and reaction tank 224, where it may be subjected to an aeration-and-heating process. While in the aeration and reaction tank 224, the volume of clarified juice syrup may be heated to a preferred temperature of about 80° C. In step 134, a quantity of flocculant (e.g., 2-4 ppm polyacrylamide) may be added to the volume of clarified juice syrup in the aeration and reaction tank 224. While in the aeration and reaction tank 224, air is used to aerate the flocculated particles so that they float to the surface of the juice syrup in the form of a froth that can be easily removed during subsequent clarification in sugar cane juice syrup clarifier 226. As will be apparent to those skilled in the art, the actual amount of flocculant needed is dependent upon how dirty the raw sugar cane is when it is initially introduced into the mills. Furthermore, the amount of flocculant required may be vary depending upon the juice flow rate. Reducing the juice flow rate (e.g., from 100 gallons/minute to 50 gallons/minute) will correspondingly reduce the amount of flocculant needed.

Preferably, in step 136, the flocculated juice syrup is maintained in clarification apparatus 226 for about 40-60 minutes, after which it is communicated to and stored in, clarified juice syrup tank 228. If desired, the juice syrup may be further clarified prior to being transferred to juice syrup tank 228 for temporary storage. Preferably, the stored clarified juice syrup has a Brix of about 65° Bx+/−5° Bx. Product testing during production runs has confirmed that the clarified juice syrup at this stage of the process has a minimum policosanol content/concentration (PC) within a range of at least about 275-300 ppm (i.e., 275-300 mg/L).

In accordance with a primary implementation, the clarified juice syrup (65° Bx+/−5° Bx) is further processed into a dry granulated sugar cane juice concentrate additive as described in greater detail below. However, in accordance with an alternative implementation, the clarified juice syrup may be further processed into a high PC sugar cane juice syrup end product.

Alternative Implementation: High Policosanol Content (PC) Syrup Concentrate

In accordance with an alternative implementation, clarified juice syrup, stored in syrup tank 228 at about 60-65° Bx, may be further processed in order to achieve a final product in the form of a high PC clarified sugar cane juice syrup concentrate that may be used, for example, as an alternative to high-fructose corn syrup commonly used as a beverage sweetener in sugary drinks.

Initially, clarified juice syrup concentrate stored in syrup tank 228 may be subjected to a final surface clarification using flocculant in much the same manner as previously described herein.

Subsequently, the clarified juice syrup concentrate may be filtered (e.g., using diatomaceous earth and carbon, and a 1-micron stainless steel mesh filter) in order to remove any remaining impurities. The carbon is preferably incorporated to improve color and turbidity of the clarified juice syrup concentrate. Following filtration, the filtered clarified juice syrup concentrate may be transferred to a post-filtration juice syrup tank—preferably, at about 65° Bx—for temporary storage.

Subsequently, the filtered juice syrup concentrate may be pumped from the filtered juice syrup tank to a vacuum evaporator, where the sucrose concentration is increased to a desired Brix value depending upon the desires of the final customer. For example, in the United States, customers generally desire a juice syrup concentrate having a Brix value of about 72° Bx, while European customers generally desire a juice syrup concentrate having a Brix value of about 76° Bx. Accordingly, the vacuum evaporation variables (e.g., vacuum level, temperature, time, etc.) are dependent upon the final desired concentration. A person having ordinary skill in the art can determine the vacuum evaporation variables with very little, if any, undue experimentation.

Unless the post-evaporated juice syrup concentrate is refrigerated, it should be subjected to an inversion process. Inversion imparts greater preservation qualities (i.e., better shelf life) and reduced crystallization in the final product. In particular, the post-evaporated juice syrup concentrate may be transferred to an inversion tank where the disaccharide sucrose is chemically converted, via hydrolysis (i.e., mixed with water and heated), into a 1:1 mixture of monosaccharide fructose and glucose. During inversion, one molecule of sucrose consumes one molecule of water. Consequently, the density of the juice syrup concentrate increases with progressing degrees of inversion, and the corresponding volume decreases. As a result, the juice syrup is further concentrated. Moreover, since fructose is the sweetest type of natural sugar, the presence of free fructose in the inverted juice syrup gives it a sweeter flavor.

Citric acid may be added to obtain a pH of 4.3+/−0.5. The addition of citric acid also helps to split the sucrose molecules into glucose and fructose. Liquid yeast (approx. 150 ppm) may be added to help initiate the inversion process. The concentrated juice syrup may then be maintained in the inversion tank at a temperature of about 60° C. for about 24 hours-until obtaining a juice sucrose content no greater than 12 percent (i.e., Pol≤12%).

Subsequently, the inverted juice syrup concentrate may be pumped to a pasteurization tank where the juice syrup concentrate is pasteurized by increasing the temperature to about 120° C. for about 3 minutes, and then reducing the temperature to about 60° C. prior to packaging for commercial sale. Pasteurization destroys any pathogenic microorganisms in the juice syrup concentrate.

Following pasteurization, the juice syrup concentrate preferably undergoes a final filtration step. The juice syrup concentrate may be filtered through a 1-micron mesh to remove and remaining particulates that may have been introduced during processing; for example, from the processing equipment or other external sources. Subsequently, the juice syrup concentrate may be packaged for commercial distribution.

Preferred Implementation: High Policosanol Content (PC) Dry Granulated Juice

In accordance with the preferred implementation (i.e., where the sugar cane juice is being processed into a dry, granulated form), in step 137, the clarified juice syrup (65° Bx+/−5° Bx) may be transferred to one or more vacuum evaporators 230 (e.g., a vacuum pan) for further concentration. In step 138, the clarified juice syrup may be subjected to evaporation in one or more vacuum evaporators 230. Preferably, the volume of clarified juice syrup is subjected to a vacuum of about 20 to 25 inches of mercury (i.e., 67.7 kPa to 84.66 kPa) and a temperature of about 100° C. to 110° C., to produce a volume of clarified juice syrup concentrated to about 90° Bx to 91° Bx. Significantly, the preferred vacuum and temperature conditions within the vacuum pan enable the volume of clarified juice syrup to be concentrated without crystallizing in the vacuum pan.

Following vacuum evaporation, in step 140, the clarified juice syrup, at 90° Bx to 91° Bx, is transferred to one or more atmospheric evaporators 230a to be further concentrated. During atmospheric evaporation, the clarified juice syrup is subjected to atmospheric pressure (i.e., about 14.7 psi, or about 101 kPa) and an increased temperature of about 128°

C. to 130° C., to produce a volume of clarified juice syrup concentrated to about 93°Bx+/−2° Bx, depending upon the sugar cane purity. Significantly, the preferred pressure and temperature conditions within the atmospheric evaporator enable the volume of clarified juice syrup to be further concentrated without crystallizing. At this stage of the process, the clarified juice syrup (concentrated to about 93° Bx+/−2° Bx) is ready to be crystallized/granulated.

Figures 5, 6:
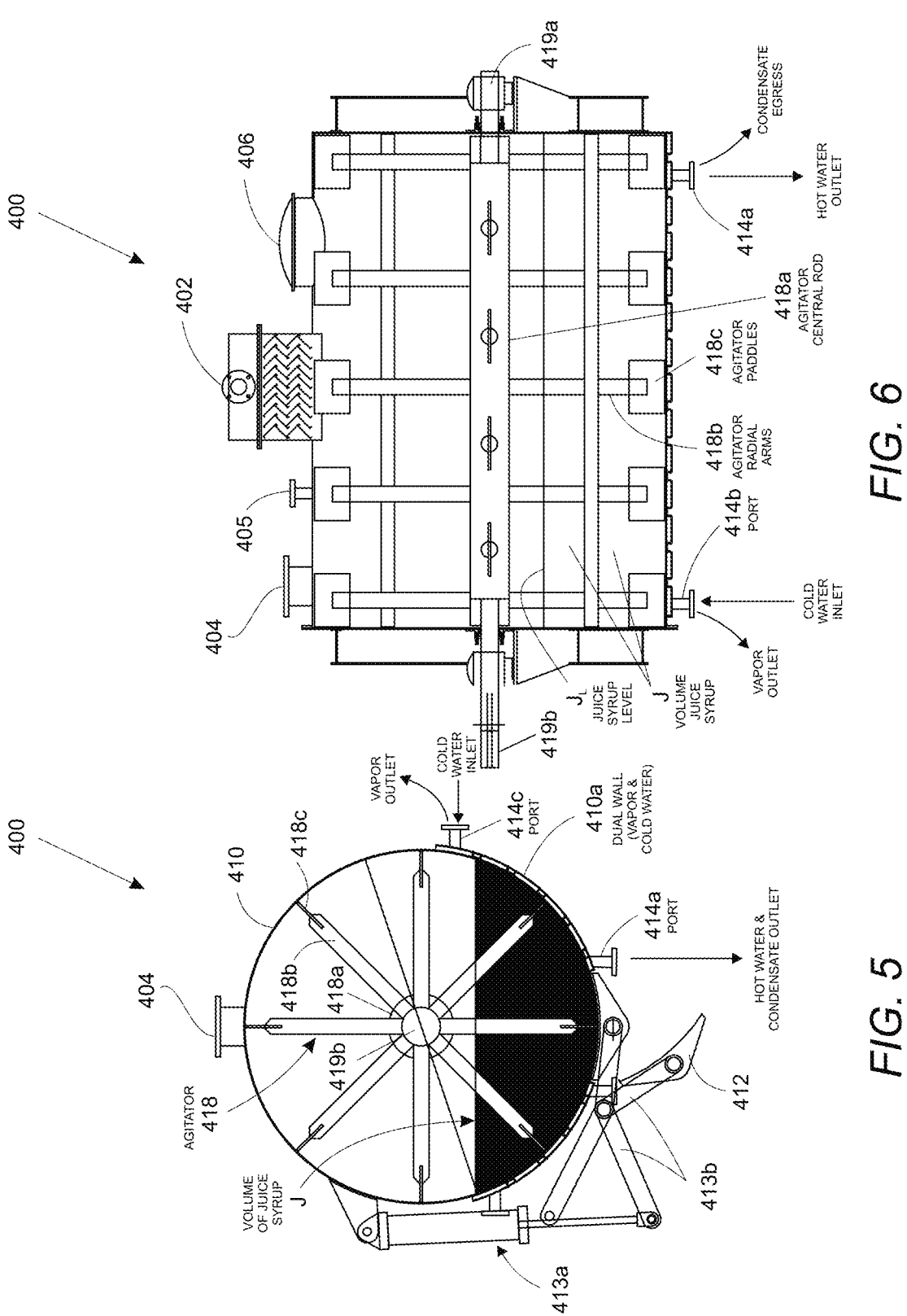
FIG. 5 is a right side/end elevation view of the crystallization apparatus 400 introduced in FIG. 3, but with the right side/end wall removed to expose the interior thereof.
FIG. 6 is a front side elevation view of the crystallization apparatus 400 introduced in FIG. 3, but with the front side wall removed to expose the interior thereof.

In step 142, the concentrated clarified juice syrup may be lowered into the crystallizer/granulation tank 400. Preferably, the crystallizer/granulation tank 400 has an interior vacuum of about 20 to 25 inches of mercury (i.e., 67.7 kPa to 84.66 kPa), and an interior temperature within a range of about 100° C. to 130° C. Low pressure steam introduced between the stainless-steel walls 410a (see FIG. 5) of the crystallizer/granulation tank body 410 maintains the interior tank temperature. Once lowered into the crystallizer tank 400, the concentrated clarified juice syrup is subjected to the aforementioned interior vacuum and temperature, while being agitated by agitator 320.

Within about 1-3 minutes after the concentrated clarified juice syrup has been lowered into the crystallizer/granulation tank 400, it begins to crystallize. This is a significant improvement over conventional crystallization using a vacuum pan, which typically takes at least 15-20 minutes before the commencement of the crystallization process. Subsequently, in steps 144 and 145, the vacuum is released, the low-pressure steam is terminated, and chilled water (i.e., preferably at a temperature of about 3° C. to 6° C.) is circulated between the stainless-steel walls 410a (See FIG. 5) of the tank body 410. As a result of these changes in the conditions within the crystallizer/granulation tank 400, an exothermic reaction occurs, wherein the concentrated clarified juice syrup, at atmospheric pressure, begins to increase in volume and form a crystallized sugar cane juice mass.

Subsequently, in step 146, the crystallized sugar cane juice mass may be gently blended within the granulation tank 400, via rotating agitation apparatus 418a-418c (see FIGS. 5-6), under heat (e.g., 125° C.+/−10° C.) until achieving a granulated sugar cane juice concentrate having a reduced humidity level, H, of 1.5% (or slightly below 1.5%). Blending of the crystallized sugar cane juice mass in the crystallizer may continue until achieving a granular volume of sugar cane juice concentrate at a desired concentration (e.g., 97.5° Bx).

Figure 13:
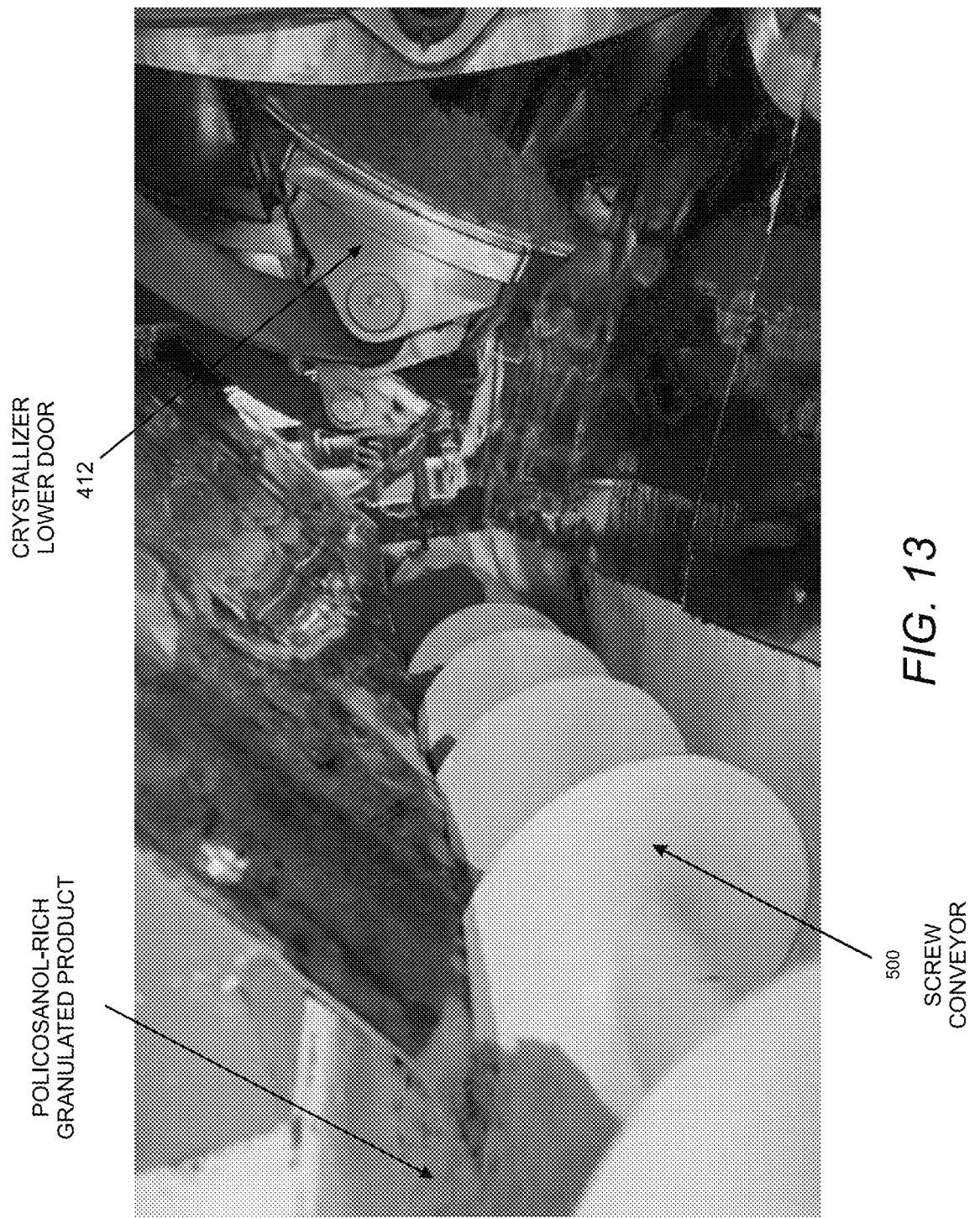
FIG. 13 is a photographic image showing the transfer of policosanol-rich dry, granulated product being conveyed, by a screw-type conveyor 500, from the crystallizer apparatus 400 to a dryer system 600 of the present invention.
Figure 14:
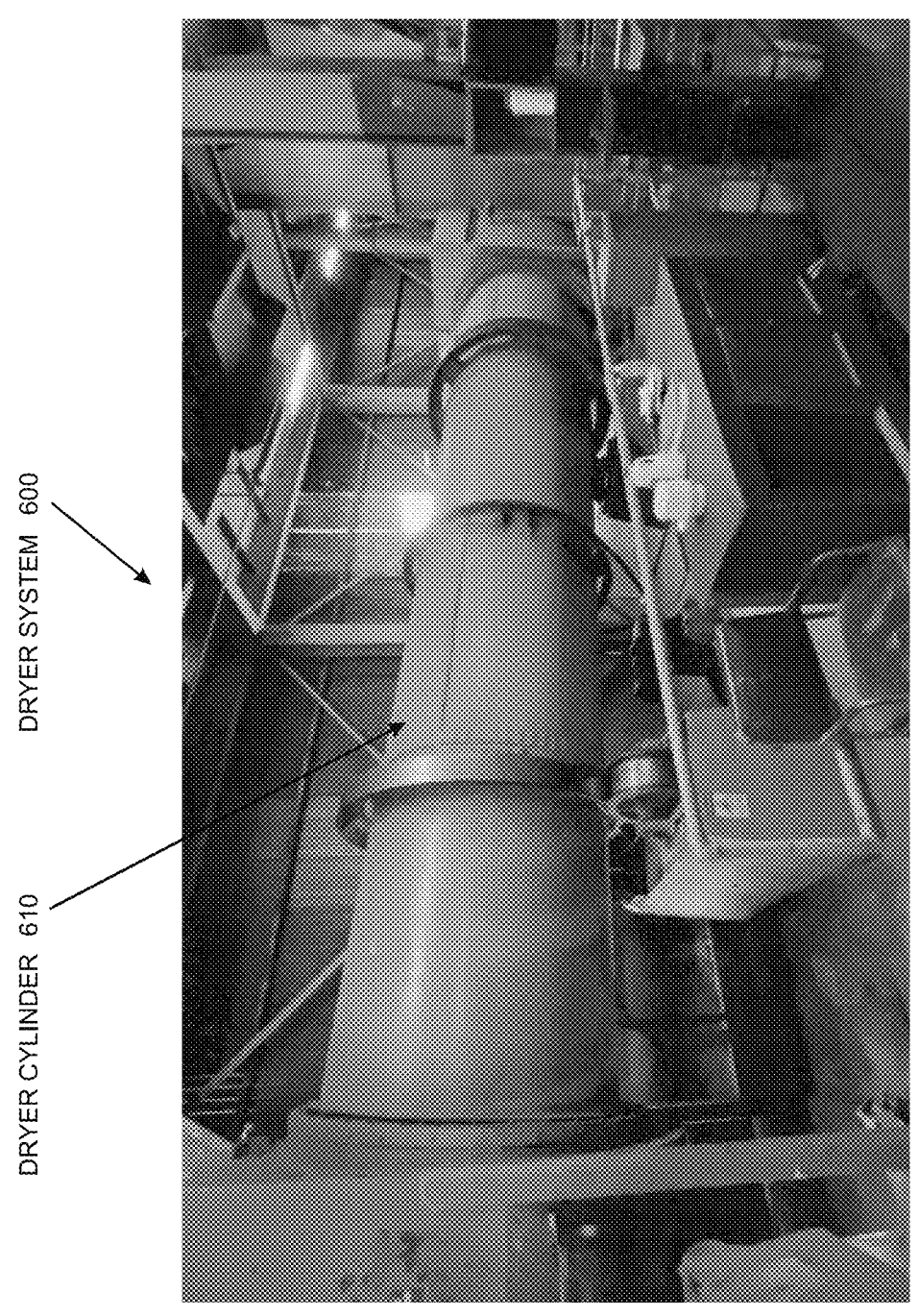
FIG. 14 is a photographic image of the exterior of a rotatable dryer cylinder 610 of the dryer system 600 of the present invention.
Figures 15A, 15B:
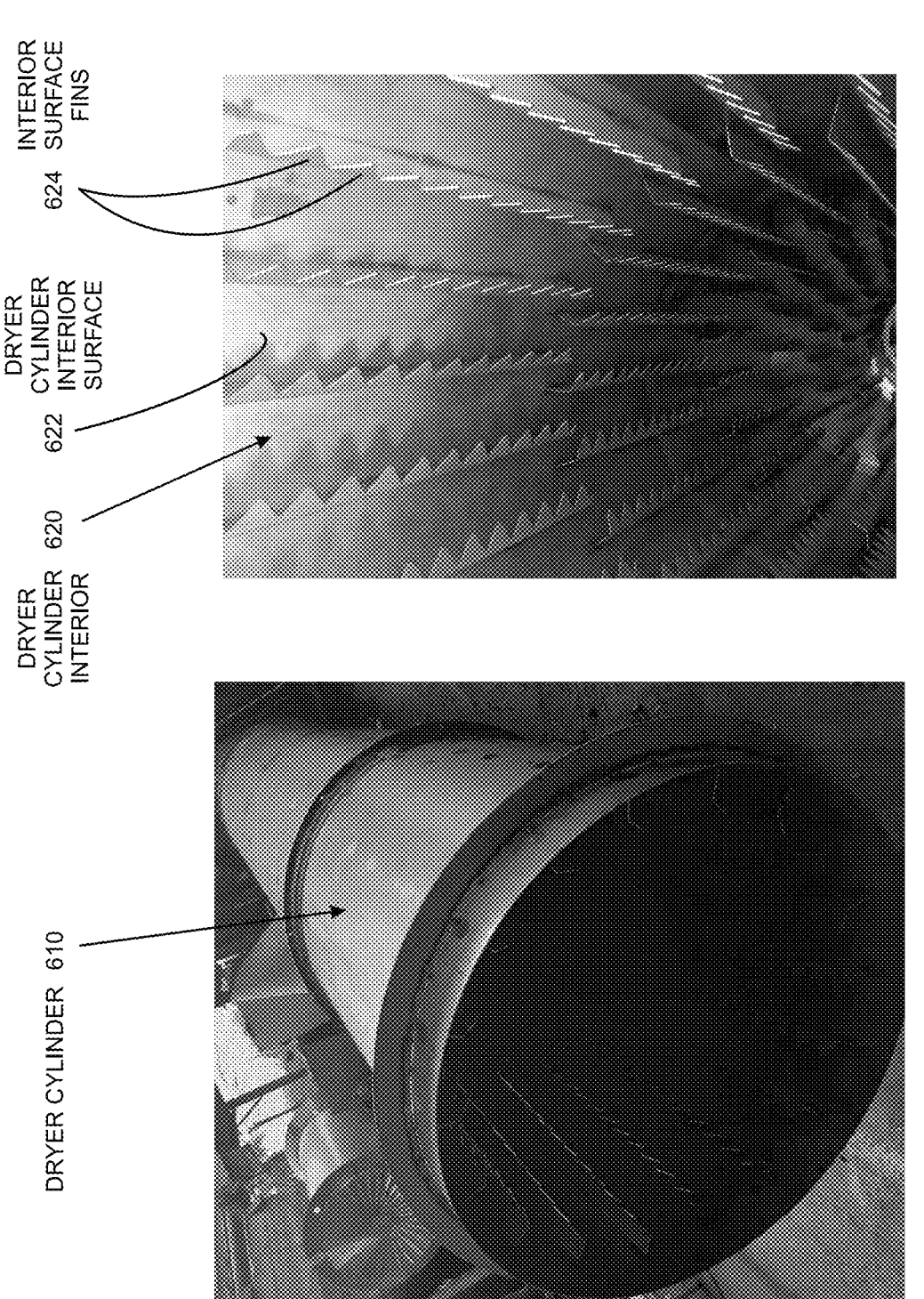
FIG. 15a is a photographic image of an open-end view of the rotatable dryer cylinder 610 shown in FIG. 14.
FIG. 15b is a close-up photographic image of the interior 620 of the rotatable dryer cylinder 610, showing details of an array of fin structures 624 extending inwardly from a dryer cylinder interior wall surface 622.

Finally, in step 148, the granulated sugar cane juice concentrate may be conveyed (e.g., by a screw conveyor 500; FIG. 13) into a low humidity dryer system 600 (FIGS. 14-15b) where the sugar cane juice concentrate granules may be gently blended under heat (e.g., approx. 50° C. to 60° C.) until achieving a final dry, granulated sugar cane juice concentrate having a further reduced humidity level, H, within a range of about 0.3% to 0.5%. Dryer system 600 includes a rotatable, elongated cylindrical dryer body 610 defining a dryer interior 620 in which the granulated product is contained. Significantly, the interior surface 622 of dryer body 610 incorporates rows of serrated teeth (i.e., longitudinally extending pointed fins 624), which function to minimize clumping of the granulated sugar product and generally aid in the drying process.

Extensive product testing has confirmed that the policosanol content (PC) in the final product is consistently at least about 200-300 mg/kg (i.e., 200-300 ppm), and more typically about 275-300 mg/kg (275-300 ppm).

While the preferred embodiments of the invention have been illustrated and described, it will be clear that the invention is not so limited. Numerous modifications, changes, variations, substitutions and equivalents will occur to those skilled in the art without departing from the spirit and scope of the present invention as described in the claims.

What is claimed is:

1. A method of crystallizing a volume of clarified sugar cane concentrate having a concentration of dissolved sugars within a range of 60° Brix to 70° Brix, the method comprising steps of:

vacuum evaporating the volume of clarified sugar cane juice concentrate at a vacuum pressure within a range of 67.7 kPa to 84.66 kPa and at a temperature within a range of 100° C. to 110° C. until the volume of clarified sugar cane juice concentrate is converted to a volume of clarified sugar cane syrup having a concentration of dissolved sugars within a range of 90° Brix to 91° Brix;

atmospherically evaporating the volume of clarified sugar cane syrup at a vacuum pressure within a range of 100 kPa to 102 kPa and at a temperature within a range of 128° C. to 130° C. until achieving a volume of clarified sugar cane syrup having a concentration of dissolved sugars within a range of 91° Brix to 95° Brix just preceding the onset of crystallization;

providing a crystallization tank apparatus, comprising:

a cylindrical tank body having a laterally-extending cylindrical primary sidewall disposed about a central axis of the cylindrical tank body and terminating at opposite end walls, together, defining a cylindrical tank body interior space, the cylindrical primary sidewall having a lower door opening extending therethrough;

an arcuate tank door configured for sealing engagement with the lower door opening extending through the cylindrical primary sidewall of the tank body, the arcuate tank door moveable between a sealed, closed state and an unsealed, opened state enabling access to the tank body interior space;

a secondary sidewall disposed about and spaced apart from an exterior surface area of the laterally-extending cylindrical primary sidewall to define a sidewall gap therebetween;

an inlet extending through the secondary sidewall and in fluid communication with the sidewall gap, and an outlet extending through the secondary sidewall and in fluid communication with the sidewall gap;

a motor-driven drive shaft extending along the central axis of the cylindrical tank body;

a laterally-extending agitation component having a central rod disposed about the motor-driven drive shaft, the central rod having a plurality of spaced arms extending radially therefrom, each of the plurality of spaced arms terminating at an agitator paddle; and a vacuum pump mounted upon an exterior surface of the cylindrical primary sidewall in fluid communication with the cylindrical tank body interior space;

introducing the volume of clarified sugar cane syrup into the cylindrical tank body interior space and subjecting the volume of clarified sugar cane syrup to a vacuum pressure within a range of 67.7 kPa to 84.66 kPa and at a temperature within a range of 100° C. to 110° C. while rotating the laterally-extending agitation component to agitate the volume of clarified sugar cane syrup, while simultaneously introducing a low pressure steam through the inlet into the sidewall gap, until the volume of clarified sugar cane syrup begins to crystallize;

simultaneously releasing the vacuum pressure within the cylindrical tank body interior space and releasing the low pressure steam in the sidewall gap through the outlet until a visible exothermic reaction commences forming an increased-volume, crystallized mass of clarified sugar cane product;

introducing chilled water in the sidewall gap, the chilled water having a temperature within a range of 3° C. to 6° C.; and gently blending the crystallized mass of clarified sugar cane juice product within the cylindrical tank body at a temperature within a range of 115° C. to 135° C. until the crystallized mass is converted to a volume of dry, granulated sugar cane juice having a humidity level of 1.5% or less.

2. The method of claim 1, further comprising, after the step of gently blending, a step of:

providing a drying apparatus comprising:

a cylindrical dryer body having an interior surface defining a dryer body interior space, an interior surface of the cylindrical dryer body having interior surface fins projecting inwardly therefrom; and a screw conveyor component extending through the dryer body interior space;

opening the arcuate tank door and transferring the volume of dry, granulated sugar cane juice from the cylindrical tank body interior space, through the lower door opening of the cylindrical primary sidewall, into the dryer body interior space; and conveying the volume of dry, granulated sugar cane juice through the dryer body interior space via the screw conveyer component while heating the dryer body interior space to a temperature within a range of 50° C. to 60° C. until the humidity level of the volume of dry, granulated sugar cane juice is reduced to a humidity level within a range of 0.3% to 0.5%.

3. The method of claim 1, wherein both the volume of clarified sugar cane concentrate and the volume of dry, granulated sugar cane juice have a policosanol content (PC) of 200 ppm to 300 ppm.

4. The method of claim 2, wherein both the volume of clarified sugar cane concentrate and the volume of dry, granulated sugar cane juice have a policosanol content (PC) of 200 ppm to 300 ppm.

* * * * *